United States Patent [19]

Schulman et al.

[11] Patent Number: 5,484,404

[45] Date of Patent: Jan. 16, 1996

[54] REPLACEABLE CATHETER SYSTEM FOR PHYSIOLOGICAL SENSORS, TISSUE STIMULATING ELECTRODES AND/OR IMPLANTABLE FLUID DELIVERY SYSTEMS

[75] Inventors: Joseph H. Schulman, Santa Clarita; Alfred E. Mann, Beverly Hills, both of Calif.

[73] Assignee: Alfred E. Mann Foundation for Scientific Research, Sylmar, Calif.

[21] Appl. No.: 239,357

[22] Filed: May 6, 1994

[51] Int. Cl.$^6$ .................................................. A61N 1/04
[52] U.S. Cl. ................................................... 604/66
[58] Field of Search .................................. 128/899, D12, 128/D13; 604/65–67, 93, 175; 607/116, 120

[56] References Cited

U.S. PATENT DOCUMENTS

| | | | |
|---|---|---|---|
| 4,373,527 | 2/1983 | Fischell | 128/260 |
| 4,484,987 | 11/1984 | Gough | 204/1 T |
| 4,494,950 | 1/1985 | Fischell | 604/66 |
| 4,627,906 | 12/1986 | Gough | 204/415 |
| 4,650,547 | 3/1987 | Gough | 204/1 T |
| 4,671,288 | 6/1987 | Gough | 128/635 |
| 4,692,147 | 9/1987 | Duggan | 604/93 |
| 4,703,756 | 11/1987 | Gough et al. | 123/635 |
| 4,781,798 | 11/1988 | Gough | 128/635 |
| 4,890,620 | 1/1990 | Gough | 128/635 |
| 5,001,054 | 3/1991 | Wagner | 435/14 |
| 5,057,084 | 10/1991 | Ensminger et al. | 604/175 |
| 5,165,407 | 11/1992 | Wilson et al. | 128/635 |
| 5,190,041 | 3/1993 | Palti | 128/635 |

*Primary Examiner*—William E. Kamm
*Attorney, Agent, or Firm*—Fitch, Even, Tabin & Flannery

[57] ABSTRACT

A replaceable catheter system provides a way to replace an implantable sensor, electrode system, and/or fluid delivery/receiving system. The replaceable catheter includes an elongated tubular catheter holder for surgical implantation in a patient. The catheter holder has an open neck at a proximal end thereof just under the patient's skin. A distal end of the catheter holder extends into a body cavity in the patient. A manually replaceable catheter is inserted through a self-sealing barrier over the open end of the catheter holder. A distal end of the replaceable catheter extends longitudinally through the catheter holder and beyond the distal end thereof to expose one or more physiological/chemical sensors, tissues stimulating electrodes, and/or a fluid delivery/receiving tube carried by or formed within the replaceable catheter. The sensors and/or electrodes are electrically connected to an electronic package including a signal coupler adjacent a signal coupler carried by the catheter holder. The signal coupler is connected to an implanted control device whereby electrical signals are transmitted to and/or from the sensor and/or electrode from the control device. The control device may include, or be connected to, an implantable fluid dispenser/analyzer for dispensing or analyzing fluid via a conduit connected through the catheter holder to an opening in the replaceable catheter.

19 Claims, 4 Drawing Sheets

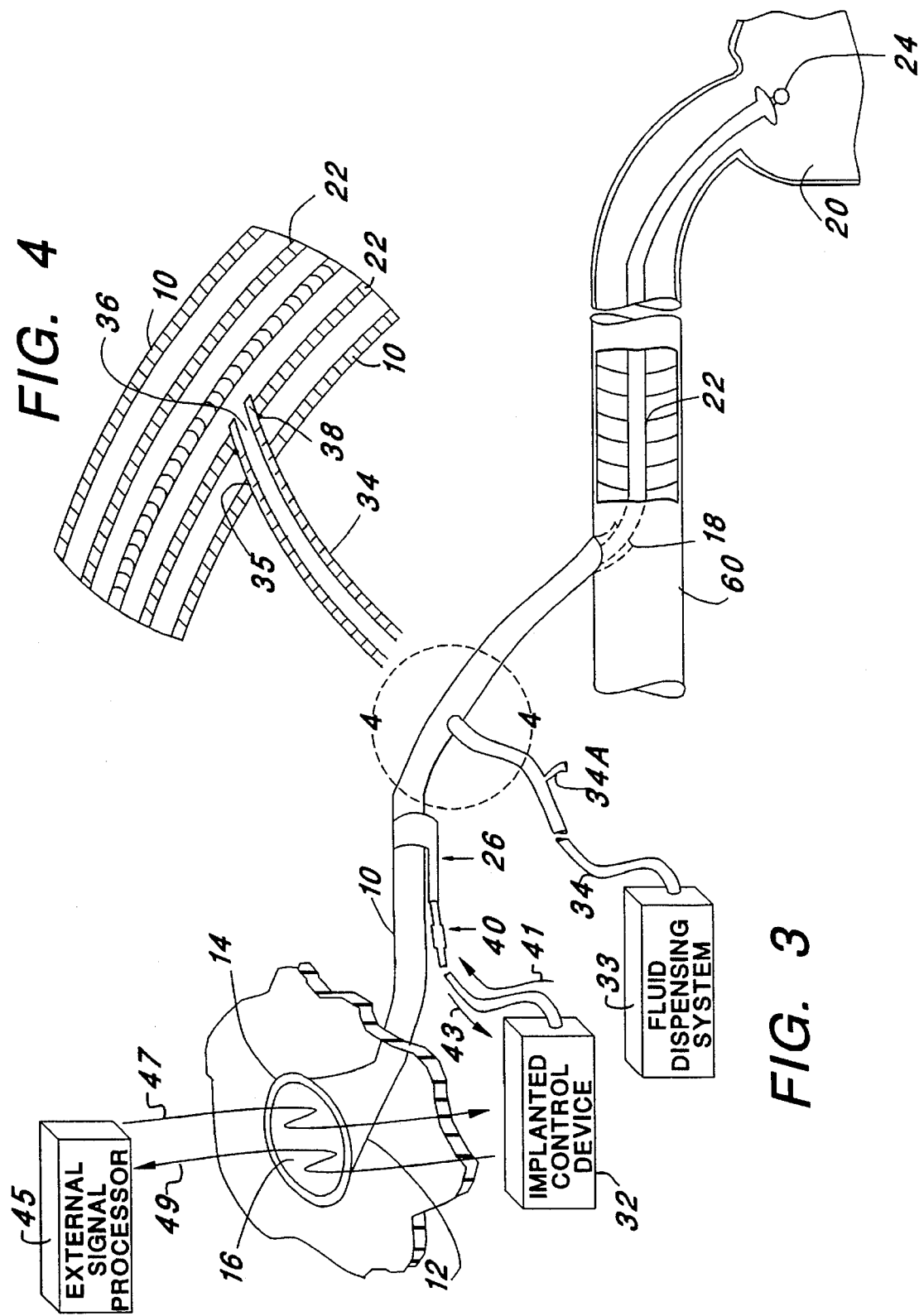

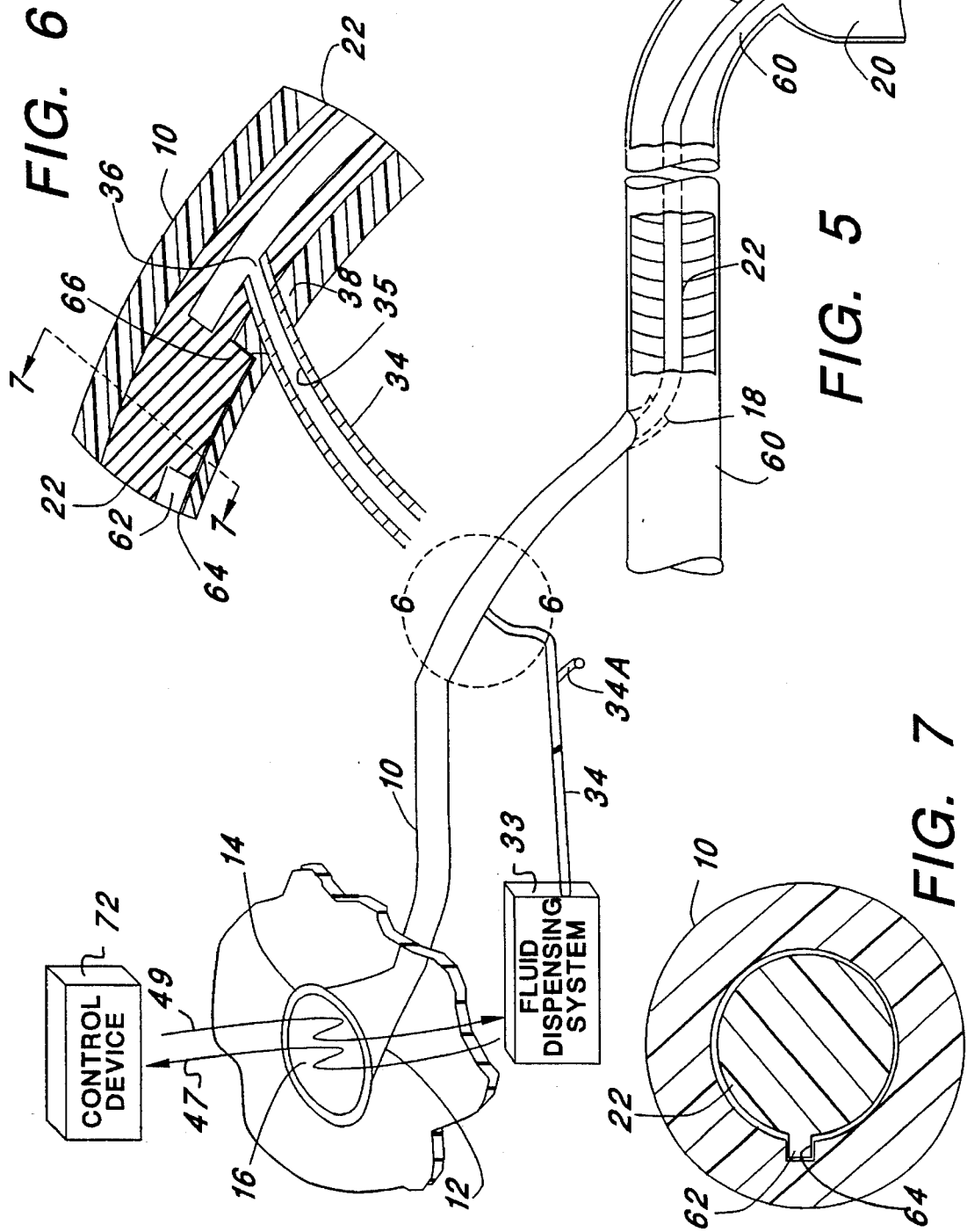

REPLACEABLE CATHETER SYSTEM FOR PHYSIOLOGICAL SENSORS, TISSUE STIMULATING ELECTRODES AND/OR IMPLANTABLE FLUID DELIVERY SYSTEMS

BACKGROUND OF THE INVENTION

The present invention relates to animal and human implantable physiological and/or chemical sensors, tissue stimulating electrodes, and/or implantable fluid delivery/receiving systems. More particularly, the invention relates to a replaceable catheter system for such sensors, electrodes and fluid delivery/receiving systems.

U.S. Pat. Nos. 4,484,987; 4,650,547; 4,781,798; 4,627,906; 4,671,288; 4,703,756; 4,890,620; 5,190,041; 5,165,407; and 5,001,054 describe various forms of glucose sensing electrodes and systems for detecting variations in and levels of glucose in blood. These patents are incorporated herein by reference.

U.S. Pat. No. 4,373,527 describes an implantable programmable medication infusion system for injecting controlled quantities of a medication such as insulin to correct for fluctuations and stabilize the level of glucose within a human in response to control information stored within the implantable system. The '527 patent is incorporated herein by reference.

U.S. Pat. No. 4,494,950 describes a medication delivery system including a plurality of modules implantable within and/or wearable by a patient. In particular, an implanted glucose sensor generates and transmits information to one or more implanted modules or modules wearable by a patient. One of the implanted modules may comprise a medication infusion system responsive to the signals from the glucose sensor module for regulating the delivery of insulin to the patient. The '950 patent also describes a system wherein a glucose sensor is connected to the end of a needle inserted through the skin of the patient and connected by an electrical lead to an external signal processing module for telemetering data to an implanted module including a medication release system for dispensing controlled amounts of medication into the patient in response to the signals from the sensor. Being attached to the tip end of the needle, the glucose sensor may be readily replaced as needed. The '950 patent is incorporated herein by reference.

While the '950 patent describes a system in which a physiological sensor on a needle tip and located just under a patient's skin is readily replaceable, surgically implanted in vivo sensors and electrodes still require surgical removal with the associated expense and risks of infection to the patient.

Accordingly, there is a continuing need for a system that allows for the implanting of physiological sensors, and/or electrodes within the body of a human in areas where it is desired to sense a predetermined physiological activity, to receive a body fluid for analysis, or to stimulate tissue; and wherein the sensor, tube, and/or an electrode may be readily replaced without engaging in an extensive, expensive and risky surgical procedure. Also, for situations where the sensor, tube, or electrode may need to be replaced frequently, e.g. every six months, while the remainder of the system with which the sensor, tube or electrode is used may last for some time, e.g. several years, it is desirable that the system accommodate replacement of only the sensor, tube or electrode portion while leaving the balance of the support system intact. Further, there is a similar need for replaceability in implantable fluid dispensing and/or receiving systems wherein fluid delivery or receiving tubes may become clogged and require replacement. In such situations, it is desirable to provide a system which allows for the non-surgical replacement of the fluid delivery/receiving tubes from the implantable fluid dispenser, such as a drug pump. The present invention satisfies such needs.

SUMMARY OF INVENTION

The present invention satisfies the needs for readily replaceable physiological or chemical sensors, fluid delivery/receiving tubes, and/or tissue stimulating electrodes, implanted within a body cavity of a patient by providing a surgically implantable elongated tubular catheter holder through which the replaceable sensors, tubes, or electrodes may be placed. The implanted catheter holder includes an enlarged open neck lying immediately under a patient's skin and covered by a self-sealing barrier or membrane. A replaceable catheter is manually insertable through the patient's skin, self-sealing barrier and neck of the catheter holder to extend longitudinally through the catheter holder. A distal end of the replaceable catheter extends beyond a distal end of the catheter holder to expose one or more physiological or chemical sensors, electrodes, and/or the distal end of a fluid delivery/receiving tube. The sensors, electrodes, and/or fluid delivery/receiving tube(s) are carried by or connected to the replaceable catheter. Further, as required, the sensors and/or electrodes are connected to an electronic package that includes circuitry for receiving and transmitting signals to and/or from the sensors and/or electrodes. Similarly, the fluid delivery/receiving tubes are connected, as required, to suitable means for dispensing or receiving a fluid through such tubes.

The circuitry included within the electronic package includes a first signal coupling means on the catheter immediately adjacent a second signal coupling means on the catheter holder for coupling signals between an implanted control device and the sensors and/or electrodes. The catheter holder and catheter include mating internal and external stop means respectively for indexing the catheter within the catheter holder such that when the catheter is fully introduced into the catheter holder, (i) the first and second signal coupling means lie immediately adjacent to each other and (ii) an opening in a side of the catheter is aligned with and sealed relative to a fluid delivery or receiving tube from an implanted fluid dispenser or analyzer. In this manner, the distal end portion of the catheter defines a replaceable extension of the delivery or receiving tube for delivering fluid to or receiving fluids from the body cavity.

Advantageously, the catheter is manually insertable through the self-sealing barrier to introduce the catheter into the implanted catheter holder. Likewise, the catheter is manually drawable from the catheter holder through the self-sealing barrier when it is desired to replace the sensors, electrodes and/or distal end of the fluid delivery/receiving tube.

BRIEF DESCRIPTION OF DRAWINGS

The above and other advantages of the present invention will be more apparent from the following more particular description thereof presented in conjunction with the following drawings, wherein:

FIG. 3 is a diagrammatic representation of one embodiment of the replaceable catheter system including an implanted medication infusion pump responsive to signals from a physiological or other sensor for controlling the dispensing of medication into the catheter for infusion into a patient;

FIG. 4 is an enlarged sectional view of the portion of the system illustrated in FIG. 3 within the circle 4—4;

FIG. 5 is a diagrammatic representation of another embodiment of the replaceable catheter system including an implanted medication infusion pump responsive to signals from an external transmitter for controlling the dispensing of medication into the catheter for an infusion into a patient;

FIG. 6 is an enlarged sectional view of the portion of the system illustrated in FIG. 5 within the circle 6—6; and FIG. 7 is an enlarged sectional view taken along the line 7—7 in FIG. 6.

Corresponding reference characters indicate corresponding components throughout the several views of the drawings.

DETAILED DESCRIPTION OF INVENTION

Figure 1:
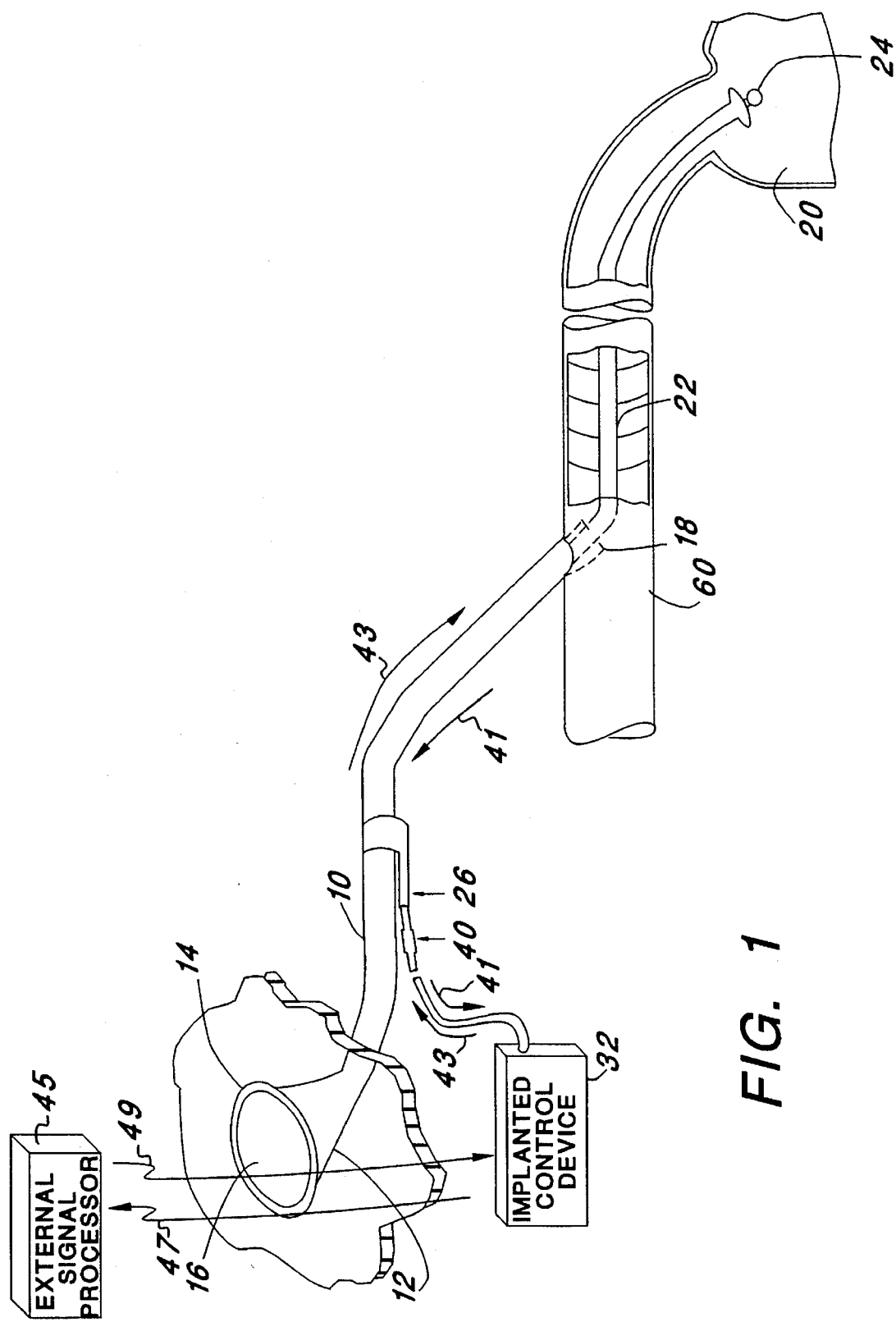
FIG. 1 is a diagrammatic representation of a replaceable catheter system in accordance with the present invention.

The following description is of the best mode presently contemplated for carrying out the invention. This description is not to be taken in a limiting sense, but is made merely for the purpose of describing the general principles of the invention. The scope of the invention should be determined with reference to the claims.

As illustrated in FIGS. 1–4 of the drawings, the replaceable catheter system of the present invention includes a surgically implantable elongated tubular catheter holder 10 formed of biocompatible material, such as silicone rubber. The catheter holder 10 includes at a proximal end thereof an enlarged open neck 12 for lying immediately under a patient's skin. An open end 13 of the neck 12 is bounded by an outer annular flange 14 which functions as an annular attachment means for a self-sealing barrier 16, such as a sheet of manually pierceable rubber-like material or membrane. A distal end 18 of the holder 10 is surgically introduceable, for example, into a branch 60 of a human or animal circulatory system or other (e.g., digestive) system to extend into a body cavity 20, or to remain in the branch 60. The branch 60 may be, for example, a vein.

An elongated tubular replaceable catheter 22 is manually insertable through the patient's skin, the self-sealing barrier 16 and neck 12 to extend longitudinally along the length of the catheter holder 10 beyond the distal end 18 and into the body cavity 20. (Alternatively, the distal end 18 may remain within the branch, e.g., vein, 60.) Along the length of the replaceable catheter 22, and/or at its distal end 18, one or more physiological or chemical sensors 24 and/or electrodes 24' are exposed to body fluids within the branch 60 or body cavity 20. These sensors 24 and/or electrodes 24' are carried by the replaceable catheter and are electrically coupled to an electronics package 26, also carried by the replaceable catheter. In one embodiment, the sensors and/or electrodes are electrically connected to a first coil 28 carried by the electronics package 26 of the catheter 22. A second coil 30, carried by the catheter holder 10, is aligned with the first coil 28 so that the two coils are inductively coupled to each other, thereby providing transformer coupling between the first coil 28 and second coil 30 so that electrical signals can readily pass therebetween.

Figure 2:
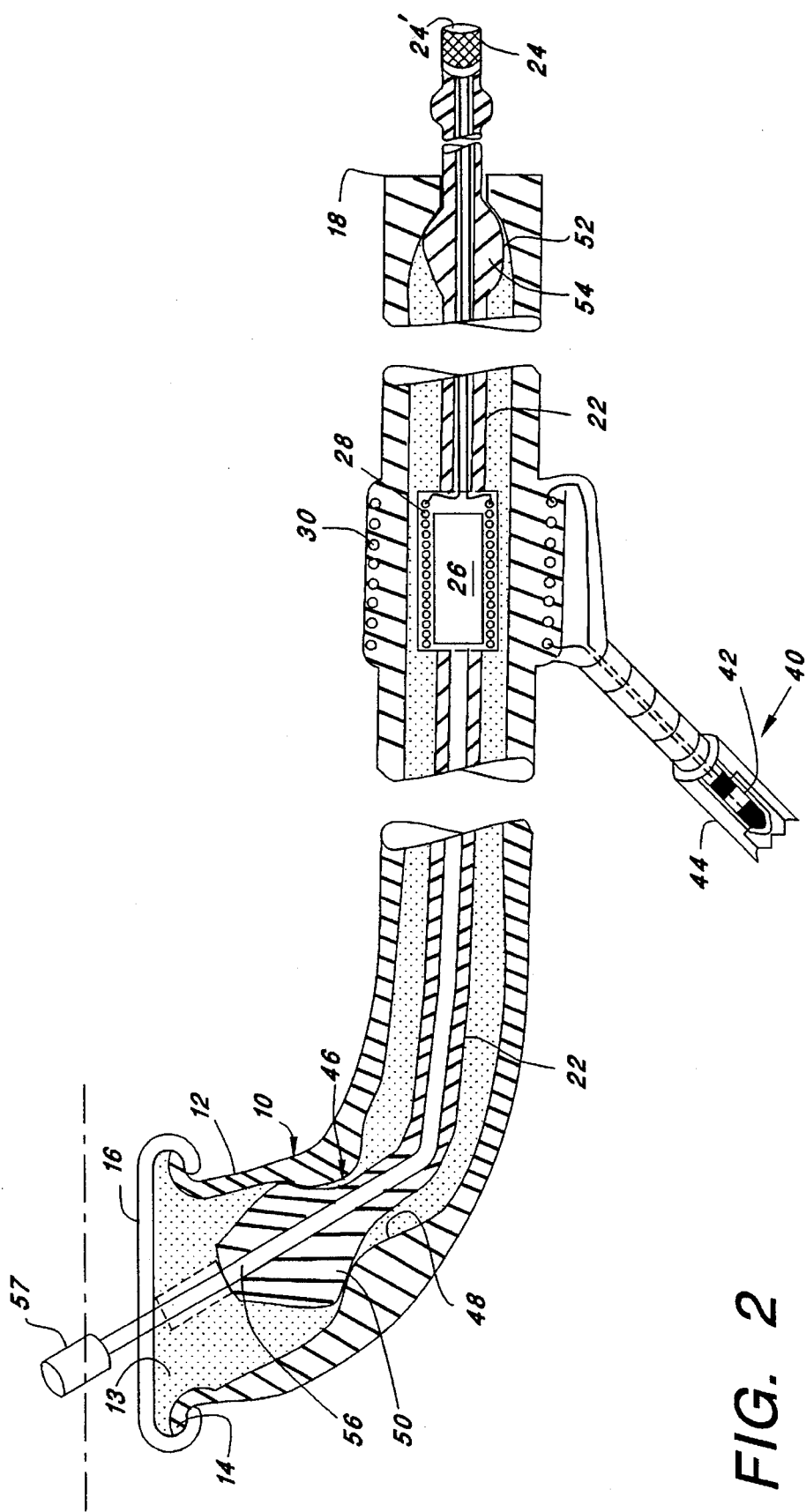
FIG. 2 is a cross sectional fragmentary view of a catheter holder and catheter comprising the catheter system of the present invention and illustrating the internal structure of the catheter holder and catheter.

The electronics package 26, which may be carried by the replaceable catheter 22 as shown, e.g., in FIG. 2, is electrically connected to the first coil 28, and includes appropriate circuitry for driving or receiving electrical signals sent to, or received from, the sensors 24 and/or electrodes 24'. For example, the circuitry within the electronics package 26 may comprise a sensor module such as the sensor module 13 described in U.S. Pat. No. 4,494,950, including a signal processor and telemetry system for sending or receiving a sensor signal via the coil 28, functioning as one transformer winding for the sensor module, to or from the coil 30, functioning as the other transformer winding. Alternatively, the electronics package 26 may comprise telemetry circuitry as described in U.S. Pat. No. 4,944,299, also incorporated herein by reference, that permits data to be transmitted between two coils in close proximity to each other at a high data rate. Advantageously, both data and power can be coupled through such windings 28 and 30. The manner of coupling power and data to and from an implanted sensor or electrode or other implanted circuitry is described, e.g., in U.S. Pat. Nos. 3,751,605; 4,741,339; or 4,809,712, all of which are incorporated herein by reference.

The coil 30 is electrically connected to an implanted control device 32 which may be similar to the intracorporeal module 15 described in U.S. Pat. No. 4,494,950. The control device 32 may include a medication release system, responsive to a sensor signal received from the sensors 24, for dispensing medication from the medication release system 33 through an output conduit 34 passing through an opening 35 in an outer wall of the catheter holder 10 to an opening 36 in an outer wall of the replaceable catheter 22, as illustrated in FIGS. 3 and 4. An end of the conduit 34 carries an annular seal 38 for surrounding the opening 36 in the catheter to provide a fluid tight seal between the conduit 34 and the replaceable catheter 22 for passing medication from the medication release system 33 into the body cavity via the replaceable catheter 22. Note, as seen in FIG. 3, that the output conduit 34 may also dispense fluid to a different location via a connecting conduit 34A. Further, in some embodiments, the control device 32 may include a suction pump for receiving fluids from the body cavity 20, in which case the conduit 34 directs or receives body fluids that are, e.g., analyzed by the control device.

As illustrated most clearly in FIG. 2, the sensor signals originate at the sensor 24, and are electrically connected to the first coil 28, carried by or on the replaceable catheter 22. The sensor signals are then coupled from the first coil 28 to the second coil 30, and to the control device 32, via a coupler 40. The coupler 40 serves the function of a connector, and comprises, by way of example, a male plug 42 electrically connected to the coil 30 and carried by a cable extending from the outer wall of the catheter holder 10, and a female socket 44 electrically connected to the implanted control device 32.

As previously indicated, sensor signals from the sensor 24 may regulate operation of the control device 32 and the medication release system 33 to provide a controlled dispensing of medication into the replaceable catheter 22 from the medication dispensing system 33 within the control device 32. Alternatively, as illustrated in FIG. 1, the sensor signal may be telemetered, as indicated by the numeral 47, to an external signal processor or control device 45, such as the module 14 described in U.S. Pat. No. 4,494,950, the output of which may be utilized to control the operation of an external medication infusion device (not shown) which introduces controlled amounts of a medication in response to the sensor signals.

Alternatively, as previously indicated, tissue stimulating electrodes 24' may be carried by the replaceable catheter 22 instead of or in addition to the sensors 24. In response to signals from a sensor or from an externally programmed device, stimulating signals may be transmitted to the implanted control device 32 and coupled via the coupler 40 and the second and first coils 30 and 28 to electrodes 24' carried by the catheter 22 to stimulate tissue within the patient.

To ensure the proper coupling of electrical signals between the first and second coils 28 and 30 and alignment of the opening 36 in the catheter 22 with the distal end of the output conduit 34 in the catheter holder 10, whereby the distal end of the catheter 22 defines a replaceable extension 25 (see FIG. 5) of the conduit 34 for delivering medication to the body cavity 20, the replaceable catheter system of the present invention preferably includes an indexing means 4=6 comprising mating stops 48 and 50 on the inside of the neck 12 and outside of a distal end of the catheter 22, respectively. The indexing means 46 may also include additional mating stops 52 and 54 located on the outside of the catheter 22 and on a distal end of the catheter holder 10, respectively, as illustrated most clearly in FIG. 2.

Alternative embodiments of the invention contemplate that other means, besides inductive coupling between the coils 28 and 30, may be used to couple the electronics package 26 with the control module 32, both for data and power transfer. For example, optical signals may be coupled between appropriate optical transmitters and receivers located on the catheter holder 10 and the replaceable catheter 22, respectively. Ultrasound signals may also be used, as may capacitive coupling, electromagnetic radiation, or direct electrical connection. Indeed, there is virtually no limitation on the type of coupling that may be used between the control module 32 and the replaceable catheter 22 in order to practice the invention. Further, it should be noted that while data is normally transferred from one or more sensors 24 to the control module 32, as indicated by arrow 41 it is also possible for data to be sent from the control module 32 to the sensor(s) 24, as indicated by arrow 43 as required, e.g., for diagnostic, control, and/or calibration purposes.

As further illustrated in FIG. 2, the replaceable catheter 22 typically carries an internal stylet insertion tool 56 comprising a relatively stiff wire. The styler tool 56 is fed through an axial opening in the replaceable catheter 22 to bear on a shoulder adjacent a sensor 24 or electrode 24' at the end of the catheter. With a handholdable tab 57 at a proximal end thereof, the stylet tool 56 guides the stiffened replaceable catheter 22 through the self-sealing barrier and open neck of the catheter holder 10 and axially there along until a distal end of the catheter 22 extends outwardly beyond a distal end of the catheter holder 10 to expose the sensors 24 or electrodes 24' carried at the distal end of the catheter within the body cavity. Conjunctively, or alternatively, additional sensors and/or electrodes may be located along the length of the replaceable catheter 22 so as to be exposed to body fluids that come in contact with such replaceable catheter along its length.

When it is desired to replace a sensor 24 or electrode 24', one simply forms a small incision in the skin over the barrier material, cuts a resealable opening in the barrier and grasps the proximal end of the catheter 22 to pull the catheter out of the catheter holder 10. A new replacement catheter 22 with sensor 24 and/or electrode 24' is then inserted in the manner previously described. Advantageously, the indexing means 48 and 50, and/or 52 and 54, may comprise mating stops that mechanically or physically engage one other, as shown in FIG. 2. Alternatively, or conjunctively, the indexing means may comprise electrical, optical or magnetic stops that electrically, optically, and/or magnetically sense the correct position of the replaceable catheter 22 with respect to the catheter holder 10.

The system illustrated in FIG. 5 resembles the system of FIG. 3 except that the dispensing system 33 is controlled by electrical signals transmitted thereto from an external control device 72. Such signals may be transmitted using conventional telemetric techniques, as disclosed, e.g., in U.S. Pat. No. 4,944,299. In response to such signals, the fluid dispenser 33 dispenses fluids through the conduit 34 into the catheter 22 in a manner similar to that described with respect to FIG. 3. Further, the structure of the coupling between the conduit 34 and the catheter 22 is as illustrated most clearly in FIG. 6. As there illustrated, the conduit 34 extends through an opening 35 in a side wall of the catheter holder 10 such that an open end 36 of the conduit 34 communicates with a side opening in the distal portion of the replaceable catheter 22. As in FIG. 4, a seal 38 extends around the conduit 34 within the opening 35 to create a fluid type seal between the conduit and the catheter holder 10.

As illustrated in FIGS. 6 and 7, the indexing means for the embodiment of the invention illustrated in FIG. 6 differs somewhat from the indexing means illustrated in FIG. 2. As shown in FIGS. 6 and 7, the indexing means comprises a fin or key 62 extending radially from and axially along a proximal portion of the catheter 22. The key 62 rides in an axially extending slot for key way 64 in an inner wall of the catheter holder 10 to function as an axial guide for the catheter 22 as it is inserted into the holder 10. Further, an end of the key way defines a radial shoulder 66 which engages an end of the key 62 to define an indexing means for the catheter 22 within the catheter holder 10.

As illustrated most clearly in FIG. 6, when the key 62 engages the shoulder 66, the open end of the conduit 34 is open to a side opening in the replaceable catheter 22 such that the distal end of the catheter 22 functions as a replaceable extension of the conduit 34 for dispensing or receiving fluids to or from the fluid dispenser/receiving unit 33 into or out of the body cavity 20.

From the foregoing, it should be appreciated that the present invention thus provides a readily replaceable catheter system for physiological or chemical sensors and/or tissue stimulating electrodes and/or fluid delivery systems which allows for the replacement of such sensors and electrodes and fluid delivery tubes without a time consuming and expensive surgical procedure.

While the foregoing specification has described preferred embodiments of the replaceable catheter system of the present invention, changes and modifications may be made in the illustrated systems without departing from the spirit of the present invention which is to be limited only by the scope of the following claims. For example, the electronics package 26 may include the transformer coupling of electrical signals between coils 28 and 30 as previously described. Alternatively, a direct electrical contact may be provided for the electrical signals to and/or from the sensors and/or electrodes, or transducers may be included in the electronics package or at the sensors or electrodes for developing light (optical) signals for transmission, as by optical fibers, and coupling to control device 32. Of course, a combination of electrical contacts, transducers, photodetectors and optical fibers may be included to develop electrical signals, convert such signals to light signals and reconvert the light signals to electrical signals for application to the electrodes or the control device, as desired.

What is claimed is:

1. A replaceable catheter system comprising:

a surgically implantable elongated tubular catheter holder having a proximal end and a distal end;

a replaceable catheter disposed within the catheter holder, the replaceable catheter having a proximal end and a distal end oriented such that the distal end of the replaceable catheter extends beyond the distal end of the catheter holder; and a means for electronically sensing and controlling prescribed physiological conditions connected to the distal end of the replaceable catheter;

whereby the electronic sensing means can be readily replaced by removing the replaceable catheter from the catheter holder, connecting another electronic sensing means to the distal end of the replaceable catheter, and inserting the replaceable catheter into the catheter holder.

2. The system of claim 1 further including:

a controlling means for operatively controlling the electronic sensing means, and a coupling means for electrically coupling the controlling means to the the electronic sensing means.

3. The system of claim 2 wherein the coupling means comprises:

first signal coupling means on the replaceable catheter for sending power signals to and receiving data from the electronic sensing means, and second signal coupling means on the catheter holder for coupling power and data signals between the controlling means and the first signal coupling means on the replaceable catheter.

4. The system of claim 3 wherein the first and second signal coupling means each comprise a coil inductively coupled to each other, thereby providing transformer coupling of electrical signals.

5. The system of claim 3 further including indexing means on the catheter holder and replaceable catheter for axially locating the replaceable catheter along the catheter holder so that the first signal coupling means is adjacent to the second signal coupling means.

6. The system of claim 5 wherein the indexing means comprises mating internal and external stops on the catheter holder and replaceable catheter, respectively.

7. The system of claim 2 further wherein the electronic sensing means further comprises a stimulating electrode.

8. The system of claim 2 further wherein the electronic sensing means further comprises a physiological sensor.

9. The system of claim 2 further wherein the electronic sensing means further comprises a chemical sensor.

10. The system of claim 2 further comprising:

a fluid dispensing means for dispensing fluids into the replaceable catheter, the fluid dispensing means electrically connected to the coupling means to receive signals from the electronic sensing means;

the replaceable catheter further having a side opening and a fluidic lumen communicating between the side opening of the replaceable catheter and the distal end of the replaceable catheter;

the catheter holder also having a side opening aligned with the side opening of the replaceable catheter; and a conduit means for passing fluids from the fluid dispensing means into the replaceable catheter in response to the signals from the electronic sensing means, the conduit means extending from the fluid dispensing means through the side opening of the catheter holder and to the side opening of the replaceable catheter, a distal end of the conduit means being in fluid communication with the side opening of the replaceable catheter.

11. The system of claim 10 further including sealing means on the distal end of the conduit means for sealing around the side opening of the replaceable catheter.

12. The system of claim 11 further including indexing means on the catheter holder and replaceable catheter for axially locating the replaceable catheter along the catheter holder with the distal end of the conduit means in sealing engagement with the side opening of the replaceable catheter.

13. The system of claim 10 further comprising an external controlling means for telemetering signals to and receiving signals from the controlling means, the external controlling means in telemetric communication with said controlling means.

14. The system of claim 1 further including at the proximal end of the catheter holder an enlarged open neck portion forming an entrance for the catheter which is easy to locate.

15. The system of claim 1 further including a self-sealing barrier over the proximal end of the catheter holder adapted to facilitate the removal and insertion of the replaceable catheter into the catheter holder.

16. A replaceable catheter system comprising:

a surgically implantable elongated tubular catheter holder having a proximal end and a distal end, said catheter holder further having an enlarged open neck portion at its proximal end forming an entrance for the catheter holder that is easy to locate, and including a self-sealing pierceable barrier covering the enlarged open neck portion, said enlarged neck portion and self-sealing pierceable barrier;

a replaceable catheter disposed within the catheter holder, the replaceable catheter having proximal end and a distal end oriented such that the distal end of the replaceable catheter extends beyond the distal end of the catheter holder;

at least one electronic sensor connected to the distal end of the replaceable catheter;

a first controlling means for operatively controlling the electronic sensor; and a signal coupling means for electrically coupling the first controlling means to the electronic sensor;

whereby the sensor can be readily replaced by removing the replaceable catheter from the catheter holder, connecting one or more other electronic sensors to the distal end of the replaceable catheter, and inserting the replaceable catheter into the catheter holder.

17. The system of claim 16 wherein said replaceable catheter system further comprises:

a fluid dispensing means for dispensing fluids into the replaceable catheter, the fluid dispensing means coupled to the controlling means wherein signals received by the controlling means from the at least one sensor are used by said controlling means to control the dispensing of fluids by the fluid dispensing means;

the replaceable catheter further having a side opening and a fluidic lumen communicating between the side opening of the replaceable catheter and the distal end of the replaceable catheter;

the catheter holder also having a side opening sealably aligned with the side opening of the replaceable catheter; and a fluid conduit means for passing fluids from the fluid dispensing means into the replaceable catheter in response to the signals from the electronic sensor, the conduit means extending from the fluid dispensing means through the side opening of the catheter holder and to the side opening of the replaceable catheter, a distal end of the fluid conduit means sealably engaged with the side opening of the replaceable catheter.

18. The system of claim 17 further comprising a second controlling means for telemetering signals to and receiving signals from said first controlling means, the second controlling means; in telemetric communication with said first controlling means.

19. A replaceable catheter system comprising:

a surgically implantable elongated tubular catheter holder having a proximal end, a side opening, and a distal end, said catheter holder further having an enlarged open neck portion at its proximal end forming an entrance for the catheter holder that is easy to locate, and including a self-sealing pierceable barrier covering the enlarged open neck portion, said enlarged neck portion and self-sealing pierceable barrier;

a replaceable catheter disposed within the catheter holder, the replaceable catheter having a proximal end and a distal end oriented such that the distal end of the replaceable catheter extends beyond the distal end of the catheter holder, the replaceable catheter further having a side opening aligned with the side opening of the catheter holder and a fluidic lumen communicating between the side opening of the replaceable catheter and the distal end of the replaceable catheter;

a replaceable extension to the replaceable catheter connected to the distal end of the replaceable catheter and adapted for dispensing and receiving fluids;

a fluid dispensing means for dispensing and receiving fluids to and from the replaceable catheter;

an external controlling means for operatively controlling the fluid dispensing means; and a conduit means for passing fluids between the fluid dispensing means and the replaceable catheter in response to the signals from the external controlling means, the conduit means extending from the fluid dispensing means through the side opening of the catheter holder and to the side opening of the replaceable catheter, a distal end of the conduit means being in fluid communication with the side opening of the replaceable catheter;

whereby the replaceable extension of the replaceable catheter can be readily replaced by removing the replaceable catheter from the catheter holder connecting a new replaceable extension to the distal end of the replaceable catheter, and inserting the replaceable catheter into the catheter holder.

* * * * *